United States Patent
Mantelle

(10) Patent No.: US 10,307,380 B1
(45) Date of Patent: Jun. 4, 2019

(54) COMPOSITION AND METHOD FOR TRANSDERMAL LIDOCAINE DELIVERY

(71) Applicant: ProSolus, Inc., San Antonio, TX (US)

(72) Inventor: Juan A. Mantelle, Miami, FL (US)

(73) Assignee: ProSolus, Inc., San Antonio, TX (US)

( * ) Notice: Subject to any disclaimer, the term of this patent is extended or adjusted under 35 U.S.C. 154(b) by 5 days.

(21) Appl. No.: 15/281,324

(22) Filed: Sep. 30, 2016

Related U.S. Application Data

(62) Division of application No. 14/636,691, filed on Mar. 3, 2015, now abandoned.

(60) Provisional application No. 61/947,688, filed on Mar. 4, 2014.

(51) Int. Cl.
  *A61K 9/70* (2006.01)
  *A61K 31/167* (2006.01)
  *B65D 65/38* (2006.01)

(52) U.S. Cl.
  CPC .......... *A61K 9/7053* (2013.01); *A61K 31/167* (2013.01); *B65D 65/38* (2013.01)

(58) Field of Classification Search
  None
  See application file for complete search history.

(56) References Cited

U.S. PATENT DOCUMENTS

| | | | |
|---|---|---|---|
| 4,725,272 A | 2/1988 | Gale | |
| 4,942,037 A | 7/1990 | Bondi | |
| 4,994,267 A | 2/1991 | Sablotsky | |
| 8,187,628 B2 | 5/2012 | Houze | |
| 2004/0018241 A1 | 1/2004 | Houze et al. | |
| 2004/0139705 A1* | 7/2004 | Kanios | A61K 9/7069 53/469 |
| 2006/0078604 A1 | 4/2006 | Kanios et al. | |
| 2009/0317452 A1 | 12/2009 | Komoda et al. | |
| 2011/0135627 A1 | 6/2011 | LaMotta et al. | |
| 2013/0224280 A1 | 8/2013 | Toth | |
| 2014/0288481 A1* | 9/2014 | Morgan | A61K 31/05 604/20 |

FOREIGN PATENT DOCUMENTS

EP  0 988 852 A2  3/2000

* cited by examiner

*Primary Examiner* — Bethany P Barham
*Assistant Examiner* — Barbara S Frazier
(74) *Attorney, Agent, or Firm* — Dority & Manning, P.A.

(57) ABSTRACT

Adhesive formulations are provides for manufacturing matrix-type lidocaine patches having improved performance, manufacturability and stability.

11 Claims, No Drawings

COMPOSITION AND METHOD FOR TRANSDERMAL LIDOCAINE DELIVERY

CROSS REFERENCE TO RELATED APPLICATIONS

The application is a divisional of U.S. patent application Ser. No. 14/636,691, filed on Mar. 3, 2015, which claims priority to U.S. Provisional Patent Application Ser. No. 61/947,688, filed on Mar. 4, 2014, both of which are incorporated herein in their entirety by reference thereto.

FIELD OF THE INVENTION

The present invention relates to transdermal matrix-type patch delivery systems for the delivery of lidocaine across dermal membranes.

BACKGROUND OF THE INVENTION

Transdermal drug delivery is a highly regarded and utilized route due to known efficacy and patient compliance. However, Formulation difficulties arise when delivery systems are formulated to optimize drug loading. With variations in drug loading come formulation concerns relating to optimization of drug delivery across and through the various epidermal layers.

Various transdermal drug delivery systems are known, including liquids, creams, lotions, salves, pastes, balms, gels, and ointments. A matrix-type patch is a typical patch embodiment, and includes a pressure-sensitive adhesive coated onto an impermeable or non-occlusive backing. The adhesive layer, which is applied to the skin, includes the active ingredient, and releases the active ingredient via passive diffusion when it is adhered to the skin.

Other inactive ingredients such as menthol have been incorporated into patches to enhance the feel and smell of the product when applied to the skin. However, menthol will often react with other ingredients used in the paten formulation, or evaporate leading to an unstable product. Compounds known as sensates have been used in cosmetics to impart a cooling or heating sensation. Examples include methanediol, methoxypropanediol, isopulegol, and vanillyl butyl ether. Unlike menthol, these compounds are not highly volatile, and thus do not suffer the same stability problems as menthol.

Topical, local, and transdermal delivery systems can also be formulated to achieve particular blood level profiles of the drug, such as steady-state blood level profiles or increasing blood level profiles, as may be desired for a particular drug or condition. The release rate of the drug can be controlled by altering the polymers used for the adhesive or by the addition of permeation enhancers, solubility enhancers, co-solvents, dispersion agents, and/or crystallization inhibitors.

U.S. Pat. No. 4,72,5,272 describes a reservoir-type for nitroglycerin where a liquid reservoir of nitroglycerine is layered adjacent to a polyisobutylene adhesive layer, between the adhesive and the impermeable backing. The nitroglycerin migrates through the polyisobutylene when the patch is applied to the skin to deliver the active ingredient.

U.S. Pat. No. 8,187,628 describes the use of acrylic-based polymers as the matrix adhesive wherein the adhesive properties, the solubility of the drug in the adhesive matrix, and the rate of migration of active ingredient through the matrix are adjusted by optimizing the acrylic mixture.

U.S. Pat. No. 4,994,267 describes a multi-polymer system in which ethylene vinyl acetate polymers, acrylic polymers, natural or synthetic rubbers and a tackifying agent are used in combination with a medicament to achieve the desired wear and drug solubility.

U.S. Pat. No. 4,942,037 describes another reservoir-type patch in which the adhesive layer is made from a synthetic rubber, namely a silicone pressure sensitive adhesive.

In spite of these advances, there remains a need for transdermal patch formulations and packaging systems that that can be easily manufactured and have excellent stability when stored for prolonged periods of time.

One object of the present invention is to provide matrix-type patches for the delivery of lidocaine to the skin.

Another object is to provide formulations that allow for the release of lidocaine at therapeutically effective levels.

Yet another object is to provide formulations that are easily manufactured, and that remain stable for prolonged periods of time.

Another object is to provide ingredients that do not suffer from the same problems as menthol, and still enhance the feel or smell of the product when incorporated in the matrix adhesive.

Still another object is to provide packaging materials that support the stability of the formulation.

SUMMARY OF THE INVENTION

The inventors have developed a lidocaine matrix patch that has excellent performance characteristics, that can be easily manufactured and that remains stable for longer periods of time that earlier formulations. In a first embodiment the invention provides a wet formulation useful for the manufacture of an adhesive matrix in a 3-5% lidocaine patch having a coat weight of from 4.0 to 6.0 mg/m$^2$, comprising (a) from about 1.0 to about 3.0 weight parts lidocaine base; (b) from about 1.5 to about 15.0 weight parts cross-linked homopolymer of N-vinyl-2-pyrrolidone; (c) from about 65 to about 95 weight of a polyisobutylene mixture comprising from 35 to 45 weight parts polyisobutylene and from 55 to 65 weight parts heptane; (d) optionally from about 8.0 to about 14.0 weight parts mineral oil; and (e) from about 1.0 to about 6.0 weight parts heptane.

In a second embodiment the invention provides a method of preparing a matrix patch comprising an adhesive matrix, a release liner and a backing layer, comprising: (a) providing from about 65.0 to about 95.0 weight parts of a mixture of 38% polyisobutylene in heptane; (b) blending said mixture of step (a) with from about 1.0 to about 6.0 weight parts of heptane to provide a blend having a target viscosity; (c) mixing said blend of step (b) with from about 1.0 to about 3.0 weight parts lidocaine base, from about 0.3 to about 0.6 weight parts methoxypropanediol, from about 0.03 to about 0.06 weight parts vanillyl butyl ether, and from about 1.5 to about 15 weight parts cross-linked homopolymer of N-vinyl-2-pyrrolidone to produce a final blended composition; (d) optionally adding from about 8 to about 14 weight parts of mineral oil to blending step (b) or mixing step (c); (e) casting the final blended composition onto a release liner; (f) evaporating said heptane from said final blended composition to form an adhesive layer; (g) applying a backing material to the adhesive layer to provide a bulk patch fabric; (h) winding said bulk patch fabric onto rolls; (i) cutting the bulk patch fabric in one or more desired shapes and sizes of patch units; and (j) individually packaging said patch units in one or more sealed pouches.

In a third embodiment the invention relates to the final patch after it has been manufactured. In this embodiment the invention provides a lidocaine patch comprising an adhesive matrix layer and a backing layer, wherein the adhesive matrix layer comprises (a) from about 3.0 to about 5.0 weight parts lidocaine base; (b) from about 3.0 to about 25.0 weight parts cross-linked homopolymer of N-vinyl-2-pyrrolidone; (c) from about 45.0 to about 94.0 weight parts polyisobutylene; and (d) optionally from about 18.0 to about 24.0 weight parts mineral oil.

A fourth embodiment relates to the use of sensates in matrix patch formulations to impart a cooling or heating effect to the product. This embodiment provides a matrix-type transdermal drug delivery system comprising an adhesive matrix layer and a backing layer, wherein said adhesive matrix layer comprises one or more sensates selected from the group consisting of methanediol, methoxypropanediol, isopulegol, and vanillyl butyl ether in an amount effective to provide a heating or cooling sensation to the skin.

A fifth embodiment relates to packaging that has been found particularly useful for the patches of the present invention. In this embodiment the invention provides a packaged matrix-type transdermal drug delivery system inside a sealed package wherein (a) said transdermal delivery system comprises an adhesive matrix layer comprising about 4% lidocaine base in a polyisobutylene adhesive matrix, a polyester cloth backing layer, and a fluorosilicon release liner; and (b) said sealed package comprises two evenly-dimensioned opposed layers of acrylonitrile-methyl acrylate copolymer sealed around their periphery.

Additional advantages of the invention are set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE PREFERRED EMBODIMENT

Definitions

When the singular forms "a," "an" and "the" or like terms are used herein, they will be understood to include plural referents unless the context clearly dictates otherwise. Thus, for example, reference to "a pharmaceutical carrier" includes mixtures of two or more such carriers, and the like. The word "or" or like terms as used herein means any one member of a particular list and also includes any combination of members of that list.

When used herein the term "about" or "ca." will compensate variability allowed for in the pharmaceutical industry and inherent in pharmaceutical products, such as differences in product strength and bioavailability due to manufacturing variations and time-induced product degradation. The term allows for any variation which in the practice of pharmaceuticals would allow the product being evaluated to be considered pharmaceutically equivalent or bioequivalent, or both if the context requires, to the recited strength of a claimed product.

Throughout the description and claims of this specification, the word "comprise" and variations of the word, such as "comprising" and "comprises," means "including but not limited to," and is not intended to exclude, for example, other additives, components, integers or steps.

As used herein, the term "pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

As used herein, "therapeutically effective amount" refers to an amount sufficient to elicit the desired biological response. The therapeutically effective amount or dose will depend on the age, sex and weight of the patient, and the current medical condition of the patient. The skilled artisan will be able to determine appropriate dosages depending on these and other factors in addition to the present disclosure.

When ranges are given by specifying a plurality of ranges that include the lower end of a range separately from the upper end of the range, it will be understood that additional ranges can be defined by selectively combining any one of the lower end variables with any one of the upper end variables that is mathematically possible.

As used herein, the term "pressure-sensitive adhesive" refers to a viscoelastic material that adheres instantaneously to most substrates with the application of very slight pressure and remains permanently tacky.

As used herein, "matrix" is defined as a polymer composition that incorporates a therapeutically effective amount of the drug therein. The matrix is typically comprised of the pressure sensitive adhesive in a matrix-type patch.

When percentages are given herein they will be understood to mean weight percentages unless indicated otherwise.

Discussion

As noted, the invention relates to formulations particularly useful as the pressure-sensitive adhesive in a matrix-type patch. The formulations are particularly useful in the manufacture of lidocaine patches comprising from about 3 to about 5%, from about 3.5 to about 4.5%, or about 4% lidocaine, having a coat weight of from about 4.0 to about 6.0, from about 4.5 to about 5.5, or about 5.0 mg/m². When the formulation is initially prepared wet, and before it is laid down onto a release liner, it preferably comprises (a) from about 1.0 to about 3.0 weight parts lidocaine base; (b) from about 1.5 to about 15.0 weight parts cross-linked homopolymer of N-vinyl-2-pyrrolidone; (c) from about 65 to about 95 weight of a polyisobutylene mixture comprising from 35 to 45 weight parts polyisobutylene and from 55 to 65 weight parts heptane; (d) optionally from about 8.0 to about 14.0 weight parts mineral oil; and (e) from about 1.0 to about 6.0 weight parts heptane.

In one embodiment the adhesive matrix comprises (a) from about 1.0 to about 2.0 weight parts lidocaine base; (b) from about 1.8 to about 2.20 weight parts cross-linked homopolymer of N-vinyl-2-pyrrolidone; (c) from about 85 to about 95 weight of a polyisobutylene mixture comprising from 35 to 45 weight parts polyisobutylene and from 55 to 65 weight parts heptane; and (d) from about 2.0 to about 6.0 weight parts heptane.

In another embodiment the adhesive matrix comprises (a) from about 1.0 to about 3.0 weight parts lidocaine base; (b) from about 5.0 to about 15.0 weight parts cross-linked homopolymer of N-vinyl-2-pyrrolidone; (c) from about 65 to about 85 weight of a polyisobutylene mixture comprising from 35 to 45 weight parts polyisobutylene and from 55 to 65 weight parts heptane; (d) from about 8.0 to about 14.0 weight parts mineral oil; and (e) from about 1.0 to about 3.0 weight parts heptane.

In one particular embodiment, the formulation for the adhesive matrix comprises (a) about 1.53 weight parts lidocaine base; (b) about 2.02 weight parts cross-linked homopolymer of N-vinyl-2-pyrrolidone; (c) about 92.2 weight parts a polyisobutylene mixture comprising 38 weight parts polyisobutylene and 62 weight parts heptane; and (f) about 3.83 weight parts heptane.

In another particular embodiment the formulation for the adhesive matrix comprises (a) about 2.06 weight parts lidocaine base; (b) about 0.52 weight parts methoxypropanediol; (c) about 0.05 weight parts vanillyl butyl ether; (d) about 11.98 weight parts cross-linked homopolymer of N-vinyl-2-pyrrolidone (e) about 72.55 weight parts a polyisobutylene mixture comprising 38 weight parts polyisobutylene and 62 weight parts heptane; (f) about 10.86 weight parts mineral oil; and (g) about 1.98 weight parts heptane.

The formulation may also include sensates to impart a hot or cold sensation to the patch applied to the skin. Thus, in another embodiment the formulation further comprises: (a) from about 0.03 to about 0.06 weight parts vanillyl butyl ether, or about 0.04 or about 0.05 weight parts vanillyl butyl ether; and from about 0.30 to about 0.60 weight parts methoxypropanediol, or about 0.38 or about 0.52 weight parts methoxypropanediol.

In a second embodiment the invention provides a method of preparing a matrix patch comprising an adhesive matrix, a release liner and a backing layer, comprising: (a) providing from about 65.0 to about 95.0 weight parts of a mixture of 38% polyisobutylene heptane; (b) blending said mixture of step (a) with from about 1.0 to about 6.0 weight parts of heptane to provide a blend having a target viscosity; (c) mixing said blend of step (b) with from about 1.0 to about 3.0 weight parts lidocaine base, from about 0.3 to about 0.6 weight parts methoxypropanediol, from about 0.03 to about 0.06 weight parts vanillyl butyl ether, and from about 1.5 to about 15 weight parts cross-linked homopolymer of N-vinyl-2-pyrrolidone to produce a final blended composition; (d) optionally adding from about 8 to about 14 weight parts of mineral oil to blending step (b) or mixing step (c); (e) casting the final blended composition onto a release liner; (f) evaporating said heptane from said final blended composition to form an adhesive layer; (g) applying a backing material to the adhesive layer to provide a bulk patch fabric; (h) winding said bulk patch fabric onto rolls; (i) cutting the bulk patch fabric in one or more desired shapes and sizes of patch units; and (j) individually packaging said patch units in one or more sealed pouches.

In a third embodiment the invention relates to the finished lidocaine patch made from the formulations and methods the present invention. This invention provides a lidocaine patch comprising an adhesive matrix layer and a backing layer, wherein the adhesive matrix layer comprises (a) from about 3.0 to about 5.0 weight parts lidocaine base; (b) from about 3.0 to about 25.0 weight parts cross-linked homopolymer N-vinyl-2-pyrrolidone; (c) from about 45.0 to about 94.0 weight parts polyisobutylene; and (d) optionally from about 18.0 to about 24.0 weight parts mineral oil.

In one preferred embodiment the adhesive layer in the finished lidocaine patch comprises (a) from about 3.0 to about 5.0 weight parts lidocaine base; (b) from about 3.0 to about 7.0 weight parts cross-linked homopolymer of N-vinyl-2-pyrrolidone; and (c) from about 84.0 to about 94.0 weight parts polyisobutylene.

In another preferred embodiment the adhesive layer in the finished lidocaine patch comprises (a) from about 3.0 to about 5.0 weight parts lidocaine base; (b) from about 19.0 to about 25.0 weight parts cross-linked homopolymer of N-vinyl-2-pyrrolidone; (c) from about 45.0 to about 60.00 weight parts polyisobutylene; and (d) from about 18.0 to about 24.0 weight parts mineral oil.

In a particularly preferred embodiment the adhesive layer in the finished lidocaine patch comprises (a) about 4.0 weight parts lidocaine base; (b) about 5.0 weight parts cross-linked homopolymer of N-vinyl-2-pyrrolidone; and (c) about 89.0 weight parts polyisobutylene.

In another particularly preferred embodiment the adhesive layer in the finished lidocaine patch comprises (a) about 4.0 weight parts lidocaine base; (b) about 22.0 weight parts cross-linked homopolymer of N-vinyl-2-pyrrolidone; (c) about 51.9 weight parts polyisobutylene; and (d) about 21.0 weight parts mineral oil.

The adhesive matrix in the final patch formulation can also include sensates, and in one embodiment the adhesive matrix further comprises: (a) from about 0.5 to about 1.5 weight parts methoxypropanediol, or about 1.0 weight parts methoxypropanediol; and from about 0.05 to about 0.15 weight parts vanillyl butyl ether, or about 0.1 weight parts vanillyl butyl ether.

A fourth embodiment relates to the use of sensates in matrix patch formulations to impart a cooling or heating effect to the formulation. This embodiment provides a matrix-type transdermal drug delivery system comprising an adhesive matrix layer and a backing layer, wherein said adhesive matrix layer comprises one or more sensates selected from the group consisting of methanediol, methoxypropanediol, isopulegol and vanillyl butyl ether in an amount effective to provide a heating or cooling sensation to the skin. In one embodiment the adhesive matrix layer comprises vanillyl butyl ether and one or more sensates selected from the group consisting of methanediol, methoxypropanediol and isopulegol. In another embodiment the adhesive layer comprises about 4% lidocaine base, from about 0.5% to about 1.5% methoxypropanediol; and from about 0.05% to about 0.15% vanillyl butyl ether. In still another embodiment the adhesive layer comprises about 4% lidocaine base, about 1.0% methoxypropanediol; and about 0.1% vanillyl butyl ether.

A fifth embodiment relates to packaging that has been found particularly useful for the patches of the present invention. In this embodiment the invention provides a packaged matrix-type transdermal drug delivery system inside a sealed package wherein (a) said transdermal delivery system comprises an adhesive matrix layer comprising about 4% lidocaine base in a polyisobutylene adhesive matrix, a polyester cloth backing layer, and a fluorosilicon release liner; and (b) said sealed package comprises two evenly-dimensioned opposed layers of acrylonitrile-methyl acrylate copolymer sealed around their periphery.

Other suitable backing materials that can be used are well known in the art and include films or sheets polyethylene, polyester, polypropylene, polyurethane, polyolefin, polyvinyl alcohol, polyvinyl chloride, polyvinylidene, polyamide, vinyl acetate resins, BAREX® ethylene/vinyl acetate copolymers, ethylene/ethylacrylate copolymers, metal-vapor deposited films or sheets thereof, rubber sheets or films, expanded synthetic resin sheets or films, non-woven fabrics, fabrics, knitted fabrics, clothes, foils and papers. These can be occlusive or non-occlusive in nature.

The release liner is utilized in a formulation to prevent loss of the active agent and/or enhancers to the environment, and render the individual unit or delivery system (in conjunction with the backing layer) transportable, as well as generally protect the dermal composition from contamination and the like until its application to a subject. The release liner is typically impermeable and occlusive, and must be compatible with the particular polymers or active agents so as not to interfere with the composition's ultimate application and therapeutic effect.

Suitable materials that can be used for the release liner are also well known in the art and include, for example, fluoropolymer and silicone coated films.

Preferably, the mixture is cast onto a release liner at room temperature at a predetermined thickness and the volatile solvent removed via a drying operation. The dermal compositions of the present invention preferably comprise the active agents solubilized therein, and attach directly to the skin after removal of the release liner.

EXAMPLES

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at room temperature, and pressure is at or near atmospheric.

Example 1

Several product samples were prepared as described in Table 1 and tested for physical performance.

TABLE 1

| | % w/w (dry) | | | | | | | | | |
|---|---|---|---|---|---|---|---|---|---|---|
| Ingredient | 1 | 2 | 3 | 4 | 5 | 6 | 7 | 8 | 9 | 10 |
| Lidocaine Base | 4 | 4 | 4 | 4 | 4 | 4 | 4 | 4 | 4 | 4 |
| Menthol | 0 | 0 | 0 | 0 | 0 | 0 | 0 | 0 | 0 | 0 |
| Bio-PSA 4202 | 96 | 0 | 0 | 0 | 0 | 48 | 0 | 24 | 0 | 0 |
| Bio-PSA 4502 | 0 | 96 | 0 | 0 | 0 | 0 | 0 | 0 | 0 | 0 |
| Bio-PSA 4602 | 0 | 0 | 96 | 0 | 48 | 0 | 48 | 0 | 0 | 0 |
| Bio-PSA 4302 | 0 | 0 | 0 | 96 | 48 | 48 | 48 | 72 | 91 | 86 |
| Kollidon VA64 | 0 | 0 | 0 | 0 | 0 | 0 | 0 | 0 | 5 | 10 |

Observations—After 10 days of standing the samples were evaluated for peel from liner and adhesive properties on a qualitative basis. The tackier capped silicone had very tight release from liner while maintaining the most adhesiveness (4302), 4202 had very little adhesion. The uncapped silicones, 4502 and 4602 also had improving adhesion accompanied by increasing blocking to the release liner. The soluble Kollidon® addition did not help with these properties but did assist in the solubilization of the drug at the 4% investigated.

Example 2

TABLE 2

| | % w/w (dry) | | | | | | | | | |
|---|---|---|---|---|---|---|---|---|---|---|
| Ingredient | 1 | 2 | 3 | 4 | 5 | 6 | 7 | 8 | 9 | 10 |
| Lidocaine Base | 5 | 10 | 20 | 10 | 10 | 10 | 5 | 10 | 20 | 20 |
| Menthol | 0 | 0 | 0 | 0 | 0 | 0 | 0 | 0 | 0 | 0 |
| *DT 87-2516 | 95 | 90 | 80 | 0 | 0 | 0 | 0 | 0 | 0 | 0 |
| *DT 87-9088 | 0 | 0 | 0 | 0 | 0 | 0 | 95 | 90 | 0 | 0 |
| *DT 87-2852 | 0 | 0 | 0 | 90 | 0 | 0 | 0 | 0 | 80 | 0 |
| *DT 87-2194 | 0 | 0 | 0 | 0 | 90 | 0 | 0 | 0 | 0 | 80 |
| *DT 87-2152 | 0 | 0 | 0 | 0 | 0 | 90 | 0 | 0 | 0 | 0 |

*DT symbolizes the Duro-Tak ® brand of adhesives from Henkel Corporation

Although the acrylic adhesives did allow for the easy release from liner and the appropriate adhesive properties, the solubility of the drug in the adhesive was very high which was considered a negative thing since more drug would have to be used to achieve the same delivery of drug to the skin.

Example 3

TABLE 3

| | % w/w (dry) | | | | | | | | | |
|---|---|---|---|---|---|---|---|---|---|---|
| Ingredient | 1 | 2 | 3 | 4 | 5 | 6 | 7 | 8 | 9 | 10 |
| Lidocaine Base | 4 | 4 | 4 | 8 | 12 | 0 | 0 | 4 | 4 | 10 |
| Menthol | 0 | 0 | 0 | 0 | 0 | 5 | 5 | 0 | 0 | 5 |
| *DT 87-608A | 86 | 88.5 | 83.5 | 82 | 78 | 0 | 0 | 0 | 0 | 0 |
| *DT 87-6908 | 0 | 0 | 0 | 0 | 0 | 82.5 | 85 | 51.5 | 83.5 | 75 |
| Mineral Oil | 10 | 7.5 | 12.5 | 10 | 10 | 7.5 | 7.5 | 22.5 | 7.5 | 5 |
| Kollidon CL-M | 0 | 0 | 0 | 0 | 0 | 0 | 2.5 | 22.0 | 5 | 5 |
| **PEG 400 | 0 | 0 | 0 | 0 | 0 | 5 | 0 | 0 | 0 | 0 |

*DT symbolizes the Henkel Corporation Duro-Tak ® line of adhesives
**PEG 400 is polyethylene glycol with an average molecular weight of 400 Daltons All formulations in this set yielded acceptable results with the exception of the one with PEG 400 which was too plasticized. The others had good potential skin wear and release from liner.

Example 4

TABLE 4

| | % w/w (dry) | | | | | | | | | |
|---|---|---|---|---|---|---|---|---|---|---|
| Ingredient | 1 | 2 | 3 | 4 | 5 | 6 | 7 | 8 | 9 | 10 |
| Lidocaine Base | 4 | 4 | 4 | 4 | 6 | 8 | 10 | 6 | 8 | 10 |
| Menthol | 0 | 0.25 | 0.5 | 1 | 1 | 1 | 1 | 5 | 5 | 5 |
| *DT 87-6908 | 83.5 | 83.25 | 83 | 82.5 | 80.5 | 78.5 | 76.5 | 76.5 | 74.5 | 72.5 |
| Mineral Oil | 7.5 | 7.5 | 7.5 | 7.5 | 7.5 | 7.5 | 7.5 | 7.5 | 7.5 | 7.5 |
| Kollidon CL-M | 5 | 5 | 5 | 5 | 5 | 5 | 5 | 5 | 5 | 5 |

TABLE 4-continued

| | % w/w (dry) | | | | | | | | | |
|---|---|---|---|---|---|---|---|---|---|---|
| Ingredient | 1 | 2 | 3 | 4 | 5 | 6 | 7 | 8 | 9 | 10 |

All formulations from this group were considered acceptable. Increased drug concentration led to increased level of saturation but the eutectic nature of the Lidocaine/Menthol mostly kept the drugs soluable.

Example 5

Tables 5 and 6 report a representative formulation of a 4% lidocaine patch of the present invention, applied at a coating weight of 5 mg/cm$^2$, to a 140 cm$^2$ patch.

TABLE 5

| Ingredient | % w/w wet | % solids | g wet for 100 g dry | % w/w in finished dry product |
|---|---|---|---|---|
| lidocaine base, USP | 1.53 | 100.0 | 4.00 | 4.0 |
| methoxypropanediol[1] | 0.38 | 100.0 | 1.0 | 1.0 |
| vanillyl butyl ether[2] | 0.04 | 100.0 | 0.1 | 0.1 |
| cross-linked homopolymer of N-vinyl-2-pyrrolidone[3] | 2.02 | 95.0 | 5.96 | 5.0 |
| polyisobutylene in heptane[4] | 92.20 | 37.0 | 240.54 | 89.0 |
| heptane | 3.83 | 0 | 10.0 | 0.0 |
| Totals: | 100.0 | N/A | 260.9 | 100.0 |
| % Solids | | | | 38.2 |

[1]Coolact 10 ™ (Tasaga/Lipo)
[2]Hotact VBE ™ (Tasaga Lipo)
[3]Kollidon CL-M ™ (BASF/Mutchler)
[4]Duro-Tak 87-6908 ™ (Henkel)

TABLE 6

| Ingredient | % w/w wet | % solids | g wet for 100 g dry | % w/w in finished dry product |
|---|---|---|---|---|
| lidocaine base, USP | 2.06 | 100.0 | 4.00 | 4.0 |
| methoxypropanediol[1] | 0.52 | 100.0 | 1.0 | 1.0 |
| vanillyl butyl ether[2] | 0.05 | 100.0 | 0.1 | 0.1 |
| cross-linked homopolymer of N-vinyl-2-pyrrolidone[3] | 11.98 | 95.0 | 23.16 | 22.0 |
| polyisobutylene in heptane[4] | 72.55 | 37.0 | 140.27 | 51.9 |
| mineral oil | 10.86 | 100.0 | 21.0 | 21.0 |
| heptane | 1.98 | 0 | 3.82 | 0.0 |
| Totals: | 100.0 | N/A | 260.9 | 100.0 |
| % Solids | | | | 51.72 |

[1]Coolact 10 ™ (Tasaga/Lipo)
[2]Hotact VBE ™ (Tasaga Lipo)
[3]Kollidon CL-M ™ (BASF/Mutchler)
[4]Duro-Tak 87-6908 ™ (Henkel)

A suitable backing for the formulation is the Sontara 8100™ polyester cloth available from DuPont. A suitable release liner is made from 9011 Supra™ (fluorosilicon) available from Saint Gobain.

Example 6

A pouch study using Barex®, Surlyn® and polyethylene packaging was conducted. The only material found that would adequately prevent the loss of the Lidocaine into the pouch was Barex®, acrylonitrile-methyl acrylate copolymer produced by Ineos, with or without foil. The Barex® liner with foil was eventually selected for additional protection as well as for the handling case during the packaging operation. After 2 months accelerated stability, the product has retained its stability, which reflects the fact that Lidocaine does not absorb onto the pouch and remains perfectly stable in the pouched units.

Throughout this application, various publications are referenced. The disclosures of these publications are hereby incorporated by reference in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A packaged matrix-type transdermal drug delivery system inside a sealed package, wherein:
    a) said transdermal drug delivery system comprises (1) an adhesive matrix layer comprising a lidocaine base in a polyisobutylene adhesive matrix, wherein the adhesive matrix layer comprises from about 3.0 to about 5.0 weight parts lidocaine base, from about 84.0 to about 94.0 weight parts polyisobutylene, and from about 3.0 to about 7.0 weight parts cross-linked homopolymer of N-vinyl-2-pyrrolidone, and (2) a non-woven fabric backing layer; and
    b) said sealed package comprises opposing layers of an acrylonitrile-methyl acrylate copolymer and foil liner.

2. The packaged transdermal drug delivery system of claim 1, wherein the adhesive matrix further comprises from about 18.0 to about 24.0 weight parts mineral oil.

3. The packaged transdermal drug delivery system of claim 1, wherein the adhesive matrix layer further comprises a sensate.

4. The packaged transdermal drug delivery system of claim 3, wherein the sensate comprises methanediol, methoxypropanediol, isopulegol, vanillyl butyl ether, or a combination thereof.

5. The packaged transdermal drug delivery system of claim 4, wherein the sensate comprises methoxypropanediol and vanillyl butyl ether.

6. The packaged transdermal drug delivery system of claim 5, wherein the adhesive matrix layer comprises from about 0.5 to about 1.5 weight parts methoxypropanediol.

7. The packaged transdermal drug delivery system of claim 5, wherein the adhesive matrix layer comprises from about 0.05 to about 0.15 weight parts vanillyl butyl ether.

8. The packaged transdermal drug delivery system of claim 1, wherein the transdermal drug delivery system further comprises a release liner.

9. The packaged transdermal drug delivery system of claim 1, wherein the non-woven fabric backing layer comprises polyethylene, polyester, polypropylene, polyurethane, polyvinyl alcohol, polyvinyl chloride, polyvinylidene, polyamide, vinyl acetate, an ethylene/vinyl acetate copolymer, an ethylene/ethylacrylate copolymer, a metal-vapor deposited film or sheet, a rubber film or sheet, a foil, paper, or a combination thereof.

10. The packaged transdermal drug delivery system of claim 9, wherein the non-woven fabric backing layer comprises polyester.

11. The packaged transdermal drug delivery system of claim 8, wherein the release liner comprises a fluoropolymer and silicone coated film.

* * * * *